United States Patent [19]

Serna

[11] Patent Number: 5,604,431
[45] Date of Patent: Feb. 18, 1997

[54] INTEGRATED GRID PARTICLE IMPACT DETECTOR

[75] Inventor: Patrick J. Serna, Albuquerque, N.M.

[73] Assignee: The United States of America as represented by the Secretary of the Air Force, Washington, D.C.

[21] Appl. No.: 536,871

[22] Filed: Sep. 29, 1995

[51] Int. Cl.$^6$ ..................................................... G01N 27/00
[52] U.S. Cl. .................................. 324/71.4; 250/385.1
[58] Field of Search .................... 250/385.1; 324/71.1, 324/71.3, 71.4

[56] References Cited

U.S. PATENT DOCUMENTS

| | | | |
|---|---|---|---|
| 3,626,189 | 12/1971 | Berg | 250/83.6 R |
| 3,694,655 | 9/1972 | Auer | 250/83.6 R |
| 3,715,590 | 2/1973 | Auer | 250/83.3 R |
| 3,853,750 | 12/1974 | Volsy | 324/71.4 |
| 3,891,851 | 6/1975 | Fletcher et al. | 250/385 |
| 4,453,226 | 6/1984 | Hobbs et al. | 324/71.4 |
| 4,491,926 | 1/1985 | Okada et al. | 324/71.4 |
| 5,153,430 | 10/1992 | Gammel et al. | 324/71.4 |
| 5,187,673 | 2/1993 | Carver | 324/71.4 |
| 5,347,130 | 9/1994 | Berthold | 250/385.1 |
| 5,376,878 | 12/1994 | Fisher | 324/71.4 |

*Primary Examiner*—Maura K. Regan
*Attorney, Agent, or Firm*—William G. Auton

[57] ABSTRACT

The Integrated Grid Particle Impact Detector (IGMID) uses an integrated semiconductor grid system to detect hypervelocity article impacts on space vehicles and to indirectly determine article diameter of impacting particles. The detector consists of multiple sets of parallel aluminum electrical paths. The first set of parallel aluminum electrical paths is located on the top surface of the detector. The second and subsequent sets are located some distance below the top surface of the detector with the paths being perpendicular and/or parallel to the first set of paths. When a particle traveling at hypervelocity impacts the detector one or more detector paths will be vaporized, resulting in an electrically open path. This in turn will result in the output of the n-type and p-type CMOS circuits to change state. Using standard CMOS VLSI design techniques, specific electrically open grid paths can be identified. With knowledge of which grid paths are electrically open, an estimate of the crater size caused by an impacting particle can be determined. Using the estimate of crater size, scaling laws and models can be used to determine an estimate of particle diameter.

4 Claims, 2 Drawing Sheets

5,604,431

INTEGRATED GRID PARTICLE IMPACT DETECTOR

STATEMENT OF GOVERNMENT INTEREST

The invention described herein may be manufactured and used by or for the Government for governmental purposes without the payment of any royalty thereon.

BACKGROUND OF THE INVENTION

This invention relates generally to a particle detection system, and more specifically the invention pertains to a system that is used to detect particles impacting on space vehicles, and to estimate impacting particle diameter.

There are many different types of space-based detection systems and observing strategies. Space-based detection systems are primarily focused on collecting data regarding the small diameter meteoroids and debris particles which cannot be detected or tracked by ground-based sensors. Examples of such systems are found in the following U.S. Patents, the disclosures of which are incorporated herein by reference:

U.S. Pat. No. 3,891,851 issued to Fletcher;
U.S. Pat. No. 3,626,189 issued to Berg;
U.S. Pat. No. 3,694,655 issued to Auer; and
U.S. Pat. No. 3,715,590 issued to Auerton.

The impact position detector of Fletcher uses many of the elements of the present invention but is used for the purpose of detecting and locating impacts. A need remains to estimate the size of impacting particles so that an accurate understanding of the space environment can be obtained. The present invention is intended to satisfy that need.

SUMMARY OF THE INVENTION

The present invention is a particle impact detection system which can produce an estimation of a cross-sectional width and cross-sectional length of impacting particles with a predetermined value of precision. This particle impact detection system uses:

a first plurality of parallel electrodes which have preselected widths and separation distances which correspond to the predetermined value of precision for said estimation of the cross-sectional widths of impacting particles;

a second plurality of parallel electrodes which are perpendicular to the first plurality of parallel electrodes. The second plurality of parallel electrodes also has preselected widths and separation distances which correspond to the predetermined value of precision for the estimation of said cross-sectional lengths of said impacting particles; a plurality of subsequent layers of pluralities of parallel electrodes which are all fixed behind the first and second pluralities of parallel electrodes, and which are connected to a monitoring means to provide thereby additional information on impacting particles thereto; and a means for monitoring particle impacts on the first and second and subsequent plurality parallel electrodes. This monitoring means determines the cross-sectional width and length of impacting particles by counting the number of parallel electrodes which are destroyed in the first, second, and subsequent plurality of parallel electrodes by impacting particles.

The monitoring means is made up of a plurality of indicator circuits which are each connected to a single parallel electrode and which output a binary indicator signal only when the parallel electrode to which the indicator circuit is connected is destroyed by an impacting particle; and a means for processing data which calculates the cross-sectional width and length of impacting particular from counting the binary indicator signals produced by the plurality of indicator circuits to produce width and length count numbers which are used with the preselected widths and separation distances of the first and second plurality of parallel electrodes to determine thereby an estimate of the size of impacting particles.

It is an object of the present invention to determine the size of debris and particles in space that pose hazards to spacecraft.

It is another object of the invention to provide a particle impact detection system which can determine the size of impacting particles.

These objects together with other objects, features and advantages of the invention will become more readily apparent from the following detailed description when taken in conjunction with the accompanying drawings wherein like elements are given like reference numerals throughout.

DESCRIPTION OF THE DRAWINGS

The invention will become more apparent from the following detailed specification and drawings in which.

DETAILED DESCRIPTION OF THE PREFERRED EMBODIMENT

The present invention is a particle impact detection system which is used to estimate the size of impacting particles using orthogonal grids of electrode strips which are placed in a stack and a counter and detection circuit.

Figure 1:
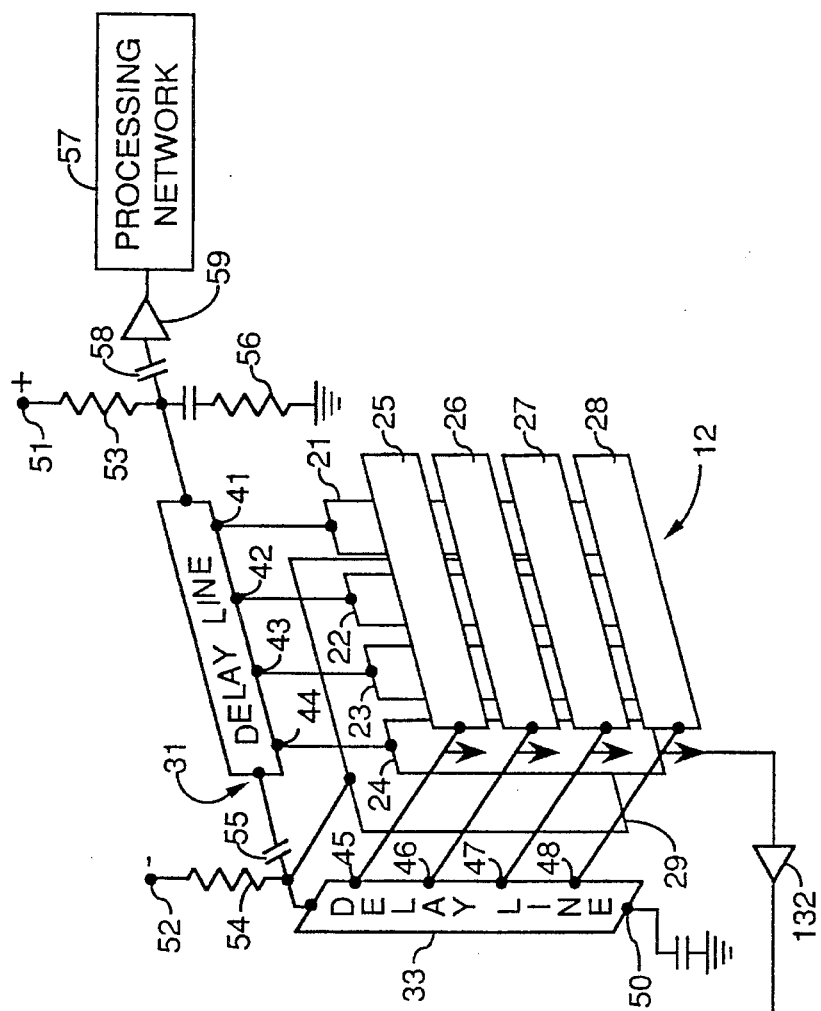
FIG. 1 is an illustration of a prior art particle impact locator system.
Figure 1:
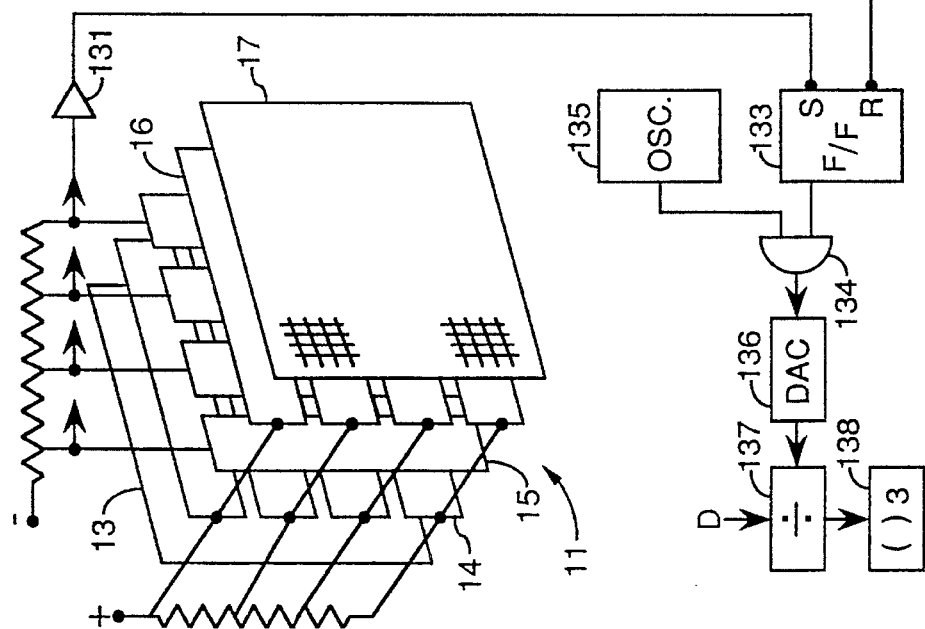

The reader's attention is now directed towards FIG. 1, which is a prior art particle detection system, which is presented to demonstrate some of the principles of particle impacts detectors that use electrode grid technology.

FIG. 1 is a partially schematic and partially perspective view of a prior art system used for particle impact location. The system of FIG. 1 has two spaced arrays 11, 12 having a common transverse axis. Array 11 is substantially the same as the five electrode configuration illustrated in U.S. Pat. No. 3,694,655 and includes five sets of electrodes 13–17 arranged in mutually parallel planes. Central electrode 15 includes a multiplicity of vertically extending, metal film strips which are connected to a positive D.C. bias voltage, whereby in response to a micrometeoroid, cosmic dust particle or other similar outer space particle impinging on the metal film, an anisotropic plasma stream is generated. The particle can also break up into several fragments which penetrate through film 15 and traverse the space between arrays 11 and 12.

To enable the plasma stream derived from electrodes 15 to be captured by array 11, without affecting the travel of particles impinging on the array 11 and enabling particles emerging from electrodes 15 to travel unimpeded to array 12, electrode screens 13, 14, 16 and 17 are located on opposite sides of electrodes 15. Electrodes 14 and 16 are formed as a multiplicity of horizontally extending screen strips, connected to a negative D.C. bias supply to collect positive ions in the plasma stream. Electrodes 13 and 17, most remote from electrodes 15, are formed as screens connected to a positive D.C. bias supply.

Electrodes 21–24 are connected to a positive D.C. bias voltage, while electrodes 25–29 are connected to a negative D.C. bias voltage. Thereby, in response to ejecta from array 11 impinging on one of electrodes 25–28, an anisotropic plasma stream or spray having positive ions and electrons therein is generated. Positively charged ions in the plasma stream derived from any of electrodes 25–28 return to the electrode from which the spray was initiated and which corresponds with line of flight of the ejecta from array 11 to electrodes 25–28 because of the attractive force between the positively charged ions and the negative D.C. voltage applied to the electrode. Because of the positive bias applied to grids 21–24, electrons in the plasma spray are collected by electrodes 21–24 in closest proximity to the impact site of the particle on electrodes 25–28 which corresponds with the line of flight of the ejecta through grid electrodes 21–24. Any electrons in the plasma spray having sufficient energy to pass through mesh electrodes 21–24 are repelled by the negative D.C. field applied to mesh electrode 29 and are returned to and/or captured by positively biased mesh electrodes 21–24.

While only four strips are illustrated as being included in the plane occupied by electrodes 21–24 and four strips are illustrated in the plane occupied by electrodes 25–28, it is to be understood that in an actual embodiment having high resolution, the number of strips in each plane is considerably in excess of four, typically being on the order of 100. The detailed description of FIG. 1 to this point is considered to be in the prior art.

To enable detection of the simultaneous impact sites of ejecta on strips 21–24 and 25–28, the spatial impact position is translated into a time position in accordance with the present invention. To this end, a delay line 31 having two series connected segments 32 and 33 is provided. Delay line segments 32 and 33 respectively include a multiplicity of tapes 41–44 and 45–48 which are connected in D.C. circuit with electrode strips 21–24 and 25–28. Positive and negative D.C. bias supply voltages are respectively connected to electrodes 21–24 and electrodes 25–28 through delay line segments 32 and 33 by D.C. sources at terminals 51 and 52 through a positive D.C. bias supply, thereby collecting electrons in the plasma stream.

Impact of a single particle on electrode 15 frequently results in the projection of solid or liquid ejecta from the impact site in the space between arrays 11 and 12. It is a primary object of the invention to determine the impact sites of the ejecta on array 12, even though the impacts occur substantially simultaneously on array 12. To enable the impact sites to be determined, array 12 includes a multiplicity of vertically extending, mutually insulated, metal, coplanar strips 21–24, having parallel longitudinal axes, approximately the same breadth and approximately equal spacing between adjacent edges of the different strips. Positioned downstream of grid electrodes 21–24 is a plurality of horizontally extending, mutually insulated coplanar, metal film electrodes 25–28, also having parallel longitudinal axes, approximately the same breadth and approximately equal spacing between adjacent edges of the different strips. Positioned upstream of grid electrodes 21–24 is a further grid electrode 29.

Electrodes 21–24 are connected to a positive D.C. bias voltage, while electrodes 25–29 are connected to a negative D.C. bias voltage. Thereby, in response to ejecta from array 11 impinging on one of electrodes 25–28, an anisotropic plasma stream or spray having positive ions and electrons therein is generated. Positively charged ions in the plasma stream derived from any of electrodes 25–28 return to the electrode from which the spray was initiated and which corresponds with line of flight of the ejecta from array 11 to electrodes 25–28 because of the attractive force between the positively charged ions and the negative D.C. voltage applied to the electrode. Because of the positive bias applied to grids 21–24, electrons in the plasma spray are collected by electrodes 21–24 in closest proximity to the impact site of the particle on electrodes 25–28 which corresponds with the line of flight of the ejecta through grid electrodes 21–24. Note that the grid electrodes of FIG. 1 structurally holds parallel strip electrodes together, but the electrodes are not electrically connected to each other.

Figure 2:
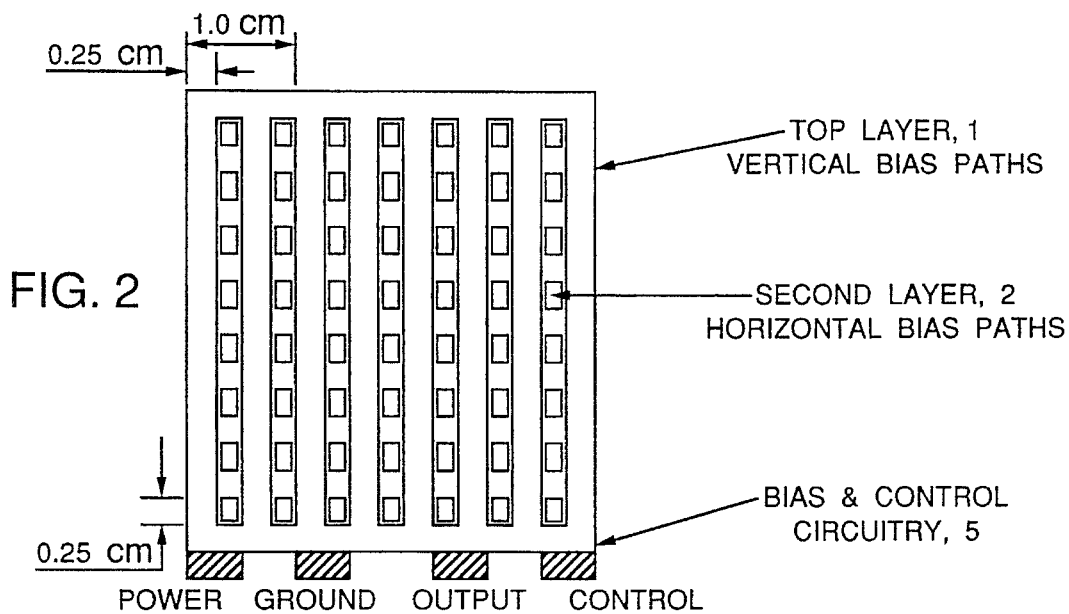
FIGS. 2 and 3 respectively present top and side views of the electrode grid systems of the present invention.
Figure 3:
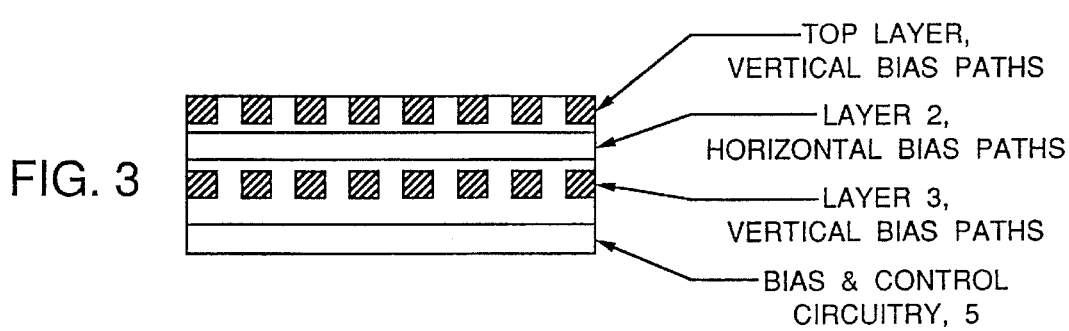

The reader's attention is now directed towards FIGS. 2 and 3 which respectively illustrate a top view and side view of the present invention, the Integrated Grid Particle Impact Detector (IGMID). The IGMID uses an integrated semiconductor grid system to detect hypervelocity particle impacts on space vehicles and to indirectly determine particle diameter of impacting particles.

The detector consists of multiple sets of parallel aluminum electrical paths. The first set 1 of parallel aluminum electrical paths is located on the top surface of the detector. The second and subsequent sets are located some distance below the top surface of the detector with the paths being perpendicular and/or parallel to the first set of paths. This configuration is shown in FIGS. 2 and 3.

Figure 4:
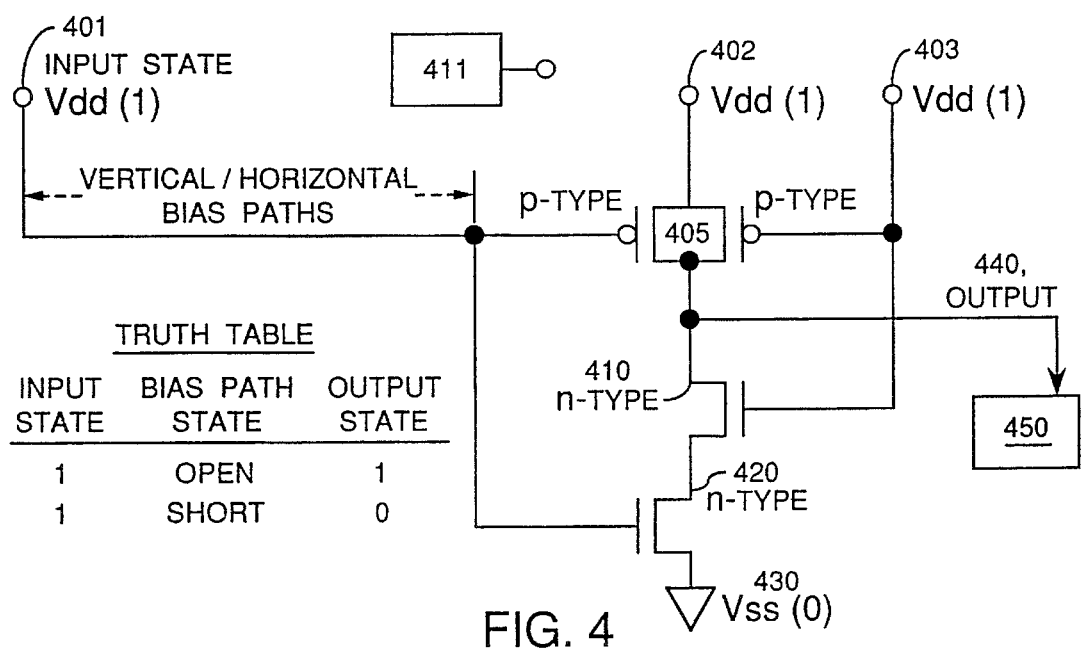
FIG. 4 is an electrical schematic view of the inverter gate (or NOT gate) circuit used with a counter in the present invention.

The detector aluminum electrical paths are used to supply an input bias to n-type and p-type CMOS circuits. When a particle traveling at hypervelocity impacts the detector one or more detector paths will be vaporized, resulting in an electrically open path. This in turn will result in the output of the n-type and p-type CMOS circuits to change state. A typical n-type and p-type CMOS circuit diagram for one bias path is shown in FIG. 4.

Using CMOS VLSI design techniques, specific electrically open grid paths can be identified. With knowledge of which grid paths are electrically open, an estimate of the crater size caused by an impacting particle can be determined. Using the estimate of crater size, scaling laws and models can be used to determine an estimate of particle diameter.

The basic element of the MOS detector system of Table 1 is a capacitor built by growing a dielectric layer of silicon dioxide on top of a doped silicon conductor layer, and then coating the silicon dioxide with a thin aluminun conductor layer. When the device is under a large bias voltage sufficiently close to the silicon dioxide's dielectric strength, a hypervelocity impact will trigger a discharge of the stored charge that will melt/vaporize a tiny area of the dielectric and vaporize a tiny area of the aluminum electrode. The voltage drop is recorded by the detection system, and the melted dielectric flows back into the crater, thus self-healing the unit. The mass (or energy) discrimination is obtained by varying the dielectric thickness. Table 1 presents the general characteristics of the MOS detector system, however variations are possible depending upon the size and environment of the particles of interest.

TABLE 1

MOS CAPACITOR
(as proposed for SYNMOD/STEMS)
PRINCIPAL SYSTEM CHARACTERISTICS

| Characteristic | |
| --- | --- |
| functional mode | electrostatic discharge |
| directionality | geometric location |
| speed & mass | limited energy sensitivity levels based on dielectric thickness |
| time resolution | design 0.5–1.0 sec |
| detectable particle size | 0.1 μm < d < few 100 μm |
| minimum useful area distributed on multiple directions | |
| detector surface | 0.1 m² |
| instrument surface | 0.2 m² |
| nominal desired area distributed on multiple directions | |
| detector surface | 1.0 m² |
| instrument surface | 1.5 m² |
| detector depth requirement | 3 mm |
| electronics space requirement | 10 × 10 × 20 cm |
| mass | |
| detector (per m²) | 5 kg |
| electronics | 1 kg |
| field of view | ~175° |
| power requirement (per m² detector area) | 1.3 W max |
| telemetry requirements | <100 kbyte/day |

As mentioned above, FIG. 4 is a schematic view of one of the CMOS circuits which works with the three grids 1–3 of FIGS. 2 and 3. The circuit of FIG. 4 has three input terminals 401–403. An output terminal 440, two n-type CMOS transistors 410, 420, two voltage bias sources 411 and 430, and two p-type CMOS transistors 405, 406 and a counter processor 450. There is a separate circuit connected to each of the electrode strips in the grids 1–3 of FIGS. 2 and 3 to allow the counter processor 450 to identify electrodes that have been disrupted by an impacting particle. The first voltage bias source 411 supplies a positive voltage Vdd to each individual electrode in grids 1–3. Each electrode is connected to an input terminal 401 of a circuit like that of FIG. 4. Table 2 (presented below) shows that the circuit of FIG. 4 outputs a binary signal 1 to the counter processor only when the electrode in the grid has been disrupted by an impacting particle. This allows a measurement of the size of the impacting particle as discussed below.

TABLE 2

TRUTH TABLE

| Input State | Bias Path State | Output State |
| --- | --- | --- |
| 1 | Open | 1 |
| 1 | Short | 0 |

If each electrode is 1.0 cm wide and separated by 0.25 cm (as shown in FIG. 2) the counter processor 450 of FIG. 4 can determine an estimate of the impacting particle's width and length as follows.

Suppose grid 1 of FIG. 2 suddenly has two adjacent electrodes destroyed by an impacting particle. That particle would need to have a width of at least 2.25 cm, but less than 3.50 cm (because a 3.50 cm width particle would shelter three electrodes.) Similarly the second grid of FIGS. 2 and 3 can yield an estimate of an impacting particles cross-sectional length, because the grid of electrode strips travel in a perpendicular direction from the top electrodes of grid 1.

Another supported feature of the invention is that the width of the electrodes and the separation distances should be selected in accordance with the desired precision of the estimate of the size of impacting particles. As mentioned above, one of the principal parameters for space vehicles, knowledge of the space environment must be obtained. Environmental models were developed to predict actual impact probabilities, however, models that generate high fidelity predictions require large and highly reliable data sets. Development of large and highly reliable particle data sets require actual measurements. To detect particles approximately 1 cm diameter the space based detector of FIG. 2 has 1 cm wide electrodes. Many space based particle detection system exist. Three key factors in any space vehicle design is the weight of the space vehicle, size of the space vehicle, and electrical power required by all electrical systems. Limitations of many of the existing space based detection systems include detector weight, size, and electrical power requirements. The detection system of FIGS. 2–4 is a lightweight method of determining the size of impacting particles.

While the invention has been described in its presently preferred embodiment it is understood that the words which have been used are words of description rather than words of limitation and that changes within the purview of the appended claims may be made without departing from the scope and spirit of the invention in its broader aspects.

What is claimed is:

1. A particle impact detection system which can produce an estimation of a cross-sectional width and cross-sectional length of impacting particles with a predetermined value of precision, said particle impact detection system comprising:

a first plurality of parallel electrodes which have preselected widths and separation distances which correspond to said predetermined value of precision for said estimation of said cross-sectional widths of said impacting particles;

a second plurality of parallel electrodes which are perpendicular to said first plurality of parallel electrodes, said second plurality of parallel electrodes having preselected widths and separation distances which correspond to said predetermined value of precision for said estimation of said cross-sectional length of said impacting particles; and a means for monitoring particle impacts on said first and second plurality of parallel electrodes, said monitoring means determining the cross-sectional width and length of impacting particles by counting the number of parallel electrodes which are destroyed in said first and second plurality of parallel electrodes by impacting particles.

2. A particle impact detection system, as defined in claim 1, further comprising a plurality of subsequent layers of pluralities of parallel electrodes which are all fixed behind said first and second pluralities of parallel electrodes, and which are connected to said monitoring means to provide thereby additional information on impacting particles thereto.

3. A particle impact detection system, as defined in claim 1, wherein said monitoring means comprises:

a plurality of indication circuits which are each connected to a single parallel electrode and which output a binary indication signal only when the parallel electrode to which the indicator circuit is connected is destroyed by an impacting particle; and a means for processing data which calculates the cross-sectional width and length of impacting particles from counting the binary indicator signals produced by the plurality of indicator circuits to produce width and length count numbers which are used with the preselected widths and separation distances of the first and second plurality of parallel electrodes to determine thereby an estimate of the size of impacting particles.

4. A particle impact detection system, as defined in claim 2, wherein said monitoring means comprises:

a plurality of indication circuits which are each connected to a single parallel electrode and which output a binary indication signal only when the parallel electrode to which the indicator circuit is connected is destroyed by an impacting particle; and a means for processing data which calculates the cross-sectional width and length of impacting particles from counting the binary indicator signals produced by the plurality of indicator circuits to produce width and length count numbers which are used with the preselected widths and separation distances of the first and second and subsequent layers of pluralities of parallel electrodes to determine thereby an estimate of the size of impacting particles.

* * * * *